United States Patent [19]

Teichmüller et al.

[11] Patent Number: 5,438,134
[45] Date of Patent: Aug. 1, 1995

[54] PROCESS FOR THE PRODUCTION OF UNSATURATED 17 α-CYANOMETHYL-17 β-HYDROXY STEROIDS

[75] Inventors: Gerhard Teichmüller; Gerd Müller, both of Jena, Germany

[73] Assignee: Jenapharm GmbH, Jena, Germany

[21] Appl. No.: 927,633

[22] PCT Filed: Jul. 5, 1991

[86] PCT No.: PCT/DE91/00562

§ 371 Date: Jun. 1, 1993

§ 102(e) Date: Jun. 1, 1993

[87] PCT Pub. No.: WO92/00991

PCT Pub. Date: Jan. 23, 1992

[30] Foreign Application Priority Data

Jul. 9, 1990 [DE] Germany .............. C 07 J3 42 603.3
Jul. 9, 1990 [DE] Germany .............. C 07 J3 42 604.1
Jul. 9, 1990 [DE] Germany .............. C 07 J3 42 605.8

[51] Int. Cl.$^6$ .......................... C07J 1/00; C07J 41/00
[52] U.S. Cl. ........................................ 540/32; 540/36; 540/37; 552/610; 552/611; 552/618; 552/619; 552/622; 552/630; 552/639
[58] Field of Search ............... 540/32, 36, 37; 552/618, 619, 622, 630, 637, 639, 610, 611

[56] References Cited

FOREIGN PATENT DOCUMENTS 0231671 12/1987 European Pat. Off. .
132497 4/1978 German Dem. Rep. .
160418 7/1983 German Dem. Rep. .
9313122 8/1993 WIPO .

OTHER PUBLICATIONS

CA119: 250245 (Abstract of Bittler).
"Immobilisation, Entgiftung und Zerstörung von Chemikalen", Dr. Dieter Martinez, Verlag Harri Deutsch, Thun Frankfurt am Main, pp. 210–211.
Steroids, Band 39, Nr. 4, Apr. 1982.
Die Pharmazie, Band 39, No. 7, 1984.
Chemical Abstracts, Band 104, No. 23, 9 Jun. 1986.
Die Pharmazie, Band 39, No. 7, 1984.
Die Pharmazie, Band 41, No. 9, 1986.
Chemical Abstracts, Band 103, No. 15, 14 Oct. 1985.
Chemical Abstracts, Band 89, No. 23, 4 Dec. 1978.
Tetrahedron, Band 28, No. 9, May 1972.
Studies in Organic Chemistry, Poznan, 9–14. Jul. 1984, No. 20, K. Schubert, et al.: "Synthesis, effects and metabolism of the progestagen . . .".
Derwent Information Research Service abstract of International Patent Appl. WO 93/13122, 1994.

*Primary Examiner*—Johann Richter
*Assistant Examiner*—Catherine S. K. Scalzo
*Attorney, Agent, or Firm*—Michael J. Striker

[57] ABSTRACT

The unsaturated 17α-cyanomethyl-17β-hydroxy steroids of the formula I,

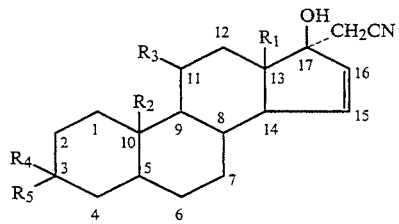

in which $R_1$=Me, Eth; $R_2$=H, Me; $R_3$=H, OH, an acetoxy or alkoxy group; $R_4$=H, $R_5$=OH, an acetoxy, alkoxy group of $R_4$ and $R_5$ together represent a keto- or ketal group and double bonds are contained in the basic structure of the steroid, particularly between the 15 and 16 position in the steroid ring, from unsaturated 17-ketosteroids of the general formula II as described herein with the aforementioned meanings of $R_1$ to $R_5$ by reacting the unsaturated 17-ketosteroids with LiCH$_2$CN and subsequently hydrolyzing.

The compounds of formula I are pharmacologically interesting steroid compounds or also intermediate products for the synthesis of highly-effective steroid products which can be used in human and veterinary medicine for the treatment of endocrine disorders and for reproductive control based on their specific hormonal/anti-hormonal actions.

The compounds are suitable for the treatment of endometriosis and also in combination with preparations with ethinylestradiol for fertility control.

33 Claims, No Drawings

PROCESS FOR THE PRODUCTION OF UNSATURATED 17 α-CYANOMETHYL-17 β-HYDROXY STEROIDS

The invention concerns unsaturated 17α-cyanomethyl-17β-hydroxy steroids, pharmaceutical preparations containing the latter, as well a a process for their production.

Unsaturated 17α-cyanomethyl-17β-hydroxy steroid derivatives are steroid compounds of pharmacological interest or also intermediate products for synthesizing pharmacologically highly-effective steroid products, e.g. 17α-cyanomethyl-17β-hydroxy-13-alkyl-4,9-gonadiene-3-one such as "Dienogest" or also17α-cyanomethyl-17β-hydroxy-13-alkyl-4,9,11-gonatriene-3-one derivatives which can be used in human and veterinary medicine in an advantageous manner for the treatment of endocrine disorders and for reproductive control based on their specific hormonal or anti-hormonal actions. A particular advantage in its application is the good compatibility of the compounds, which also produce hardly any unwanted side effects in increased dosages and also represent a desirable enrichment of the range of steroid ingredients of pharmacological interest in comparison to the known 17α-ethinyl-17β-hydroxy steroids.

The introduction of an additional double bond in these 17α-cyanomethyl-17β-hydroxy steroids in the $C_{15}/C_{16}$ position of the basic structure of the steroid leads to a significant increase in effectiveness. A series of these new derivatives show particularly favorable dissociations of characteristic partial effectiveness.

According to the invention, the new unsaturated 15-dehydro-17α-cyanomethyl-17β-hydroxy steroids of the invention have a ring structure as shown in formula I below:

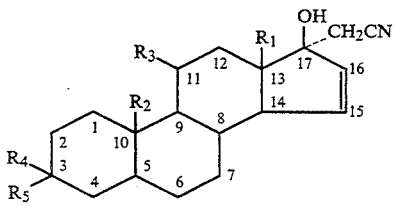

wherein
$R_1$ is methyl or ethyl;
$R_2$ is selected from the group consisting of hydrogen and methyl;
$R_3$ is selected from the group consisting of hydrogen, hydroxy, actoxy and alkoxy having 1 to 6 carbon atoms, or
$R_4$ is hydrogen and $R_5$ is selected from the group consisting of hydroxy, acetoxy and alkoxy having 1 to 6 carbon atoms, or
$R_4$ and $R_5$ are both methoxy or both ethoxy, or
$R_4$ and $R_5$, together, represent a keto group or a ketal group selected from the group consisting of —O—CH$_2$—CH—O—; —O—CH$_2$—C(CH$_3$-)$_2$—CH$_2$—O—; and —OCH(CH$_3$)—CH$_2$—CH(CH$_3$)—O—;

The new steroids of formula (I) also have at least one other double bond in the ring structure between the 1 and 2 positions, the 2 and 3 positions, the 3 and 4 positions, the 4 and 5 positions, the 5 and 6 positions, the 5 and 10 positions, the 9 and 10 positions and the 9 and 11 positions, the 1,2,3,-4,5,6,9,10 and 11 positions being shown in formula I above, with the proviso that $R_2$ cannot be methyl, when there is a double bond between the 5 and 10 positions or the 9 and 10 positions.

Dosages up to a maximum of 2 mg of active ingredient per day are advantageous in the application of these new compounds for controlling fertility. These new compounds are administered in combination with estrogen-active steroids such as ethinyl estradiol in the known pharmaceutical preparation forms as tablets or capsules.

Another area of use of the new active ingredients is the treatment of special diseases, e.g. the treatment of endometriosis. The dosage is up to 2 mg per day over a period if 4 to 6 months in this case also. These low dosages show the superiority of the new compounds particularly clearly while, according to the conventional treatment of these indications with danazol, the dosage is 400 to 800 mg of danazol daily.

The synthesis of 17α-cyanomethyl-17β-hydroxy steroids has been described in a series of patents. According to the latter, 17-ketosteroids are converted in a multiple-step synthesis into the steroid-17β-spiro-1',2'-oxirane which is then converted with alkali cyanide into 17α-cyanomethyl-17β-hydroxy steroid derivatives. According to K. Ponsold, et al., DD-PS 132 497, 3-methoxy-13-alkylgona-2,5(10)-diene-17β-spiro-1',2'-oxiran (produced according to DD-PS 80 023) is converted into 17α-cyanomethyl-17β-hydroxy-13-alkyl-gon-5(10)-en-3-one by reacting with alkali cyanide and subsequent enol-ether hydrolysis. An improvement of this synthesis was described by K. Ponsold, et al. in DD-WP 160 418, according to which the unstable starting material of the aforementioned process (DD-WP 132 497) is replaced by 3,3-dimethoxy-13-alkylgon-5(10)-en-3-one which is then converted in the same manner with trimethylsulfonium iodide, alkali cyanide and subsequent ketal cleavage into the 17α-cyanomethyl-17β-hydroxy-13-alkylgon-5(10)-en-3-one.

Although the individual steps of this synthesis have high yields, the overall efficiency is burdened by the use of expensive reagents and the high cost of labor brought about by the costly intermediate isolations.

The chief disadvantage of this process, however, consists in the high environmental loading involved in this synthesis caused by the use of

- trimethylsulfonium iodide, which requires that the waste gas and waste water be disposed of,
- alkali cyanide, a poison of Section 1 of the regulations concerning poison, which places special demands on processing on a technical scale and requires special disposal of the waste gas ad waste water.

EP 231 671 of Jun. 19, 1986, E. Nitta, et al., describes the synthesis of 17α-cyanomethyl-17β-hydroxy-13-alkylgona-4,9,11-triene-3-one derivative from the corresponding 17-ketosteroids accompanied by the use of the reaction sequence described by K. Ponsold et al.. (DD-WP 160 418): —17-ketosteroid→17β-spiro-1',2'-oxiran →17β-cyanomethyl-17β-hydroxy steroid derivatives. Although new compounds of the 17α-cyanomethyl-17β-hydroxy steroid type were described by this patent, no improvements of the original synthesis path could be disclosed, i.e. the aforementioned defects of the high cost of labor and the high environmental loading also exist in this process. The continuous additional high costs for the disposal of waste products, waste water and waste gas with sulfur compounds and cyanide in the technical implementation of this synthesis are added to the aforementioned high costs for carrying out this synthesis, adding substantial additional encumbrances to the efficiency of the overall process.

The aim of the invention is the synthesis of new pharmacologically highly-effective 17α-cyanomethyl compounds which have a significant increase in effect or additionally improved dissociation of the characteristic partial effects compared with the known 17α-cyanomethyl-17β-hydroxy steroid derivatives and can therefore be used more advantageously for the treatment of endocrine disorders and for reproduction control in human and veterinary medicine due to their improved specific effects.

It is also the aim of the invention to develop synthesis methods for the production of these new highly-effective 17α-cyanomethyl derivatives requiring the lowest possible labor costs and preventing environmental loading to the greatest extent.

The invention has the object of synthesizing new pharmacologically highly-effective 17α-cyanomethyl-17β-hydroxy steroid derivatives and providing a process according to which the aimed for products can be made accessible in a technically simple and economically favorable manner and the cost for secondary processes, particularly waste products elimination/disposal of waste water and waste gas can be minimized as far as possible.

This object is met, according to the invention, in that unsaturated 17-ketosteroids of the formula II, in which the radicals $R_1$ = Me, Eth $R_2$ = Me, H, $R_2$ is omitted when there is a doublebond at $C_{10}$ $R_3$ = H, OH, acetoxy with 1 to 6 carbon atoms, $R_4$ = H $R_5$ = OH, acetoxy, alkoxy groups with 1 to 6 carbon atoms, or $R_4$ and $R_5$, together, can represent a keto or ketal group, where $(CH_3O)_2$, $(CH_3CH_2O)_2$, —O—CH$_2$—CH$_2$—O—; —O—CH$_2$—(Me)C(Me)—CH$_2$—O—; —O—CH(Me)—CH$_2$—(Me)CH—O— can stand for the ketal group and there can be double bonds in the basic structure of the steroid molecule in positions $C_1$=$C_2$, $C_2$=$C_3$, $C_3$=$C_4$; $C_4$=$C_5$; $C_5$=$C_6$; $C_5$=$C_{10}$; $C_9$=$C_{10}$; $C_9$=$C_{11}$ and $C_{15}$=$C_{16}$, are converted in a single-vessel process in inert organic solvents at low temperatures with LiCH$_2$CN which is prepared in situ from CH$_3$CN by reacting with lithium alkyls or lithium dialkylamides (alkyl=$C_1$ to $C_6$). The reaction products are worked up with water. The new steroid compounds of the general formula I in which the radicals $R_1$ to $R_5$ have the aforementioned designation and there can be double bonds in the aforementioned positions of the basic ring structure of the steroid, are isolated or obtained by direct acid hydrolysis.

The in-situ metallization of the acetonitrile with lithium alkyls or lithium dialkylamides to form LiCH$_2$CN and its subsequent reaction in a single-vessel process with unsaturated 17-ketosteroids to form the unsaturated 17α-cyanomethyl-17β-hydroxy steroids is effected in inert organic solvents such as aliphatic or aromatic hydrocarbons, preferably pentane, hexane, heptane, benzene, toluene etc. Ethers, preferable diethyl ether, diisopropyl ether, tetrahydrofuran, dioxane, anisole, methyl t-butyl ether dimethoxyethane, diethoxyethane etc. or also in tertiary amines, e.g. triethylamine, diisopropylethylamine, pyridine, tetraalkyl ethylenediamine etc. or these solvents can also be used as mixtures.

According to the process according to the invention, 1 to 5 moles of acetonitrile and 1 to 5 moles of lithium alkyl or lithium dialkylamide are used per mole of unsaturated 17-ketosteroid in such a way that the acetonitrile is converted in situ at low temperatures with the utilized lithium derivatives into the LiCH$_2$CN and the latter is reacted with the unsaturated 17-ketosteroid to formunsaturated 17α-cyanomethyl-17β-hydroxy steroid.

This process also includes the in-situ preparation of the LiCH$_2$CN in the presence of the unsaturated 17-ketosteroid and the secondary reaction with the unsaturated 17-ketosteroid to formthe unsaturated 17α-cyanomethyl-17β-hydroxy derivative can run its course virtually simultaneously.

This process also consists in that the reactions of the alkyl lithium with the acetonitrile can also be carried out in the presence of lithium halides, i.e. in that the separation of the Li-Hal prior to further use of the alkyl lithium is not required and the presence of lithium halide does not disturb the implementation of the subsequent reactions. These reactions are advantageously carried out at low temperatures, i.e. in temperature ranges under +/− 0 degrees C., at which the reaction of the LiCH$_2$CN with acetonitrile to form β-ketopropionitrile

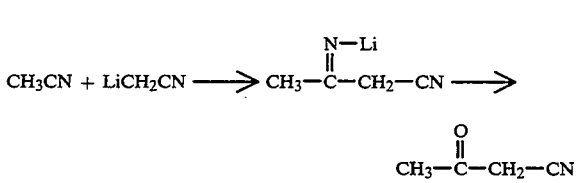

is suppressed extensively or completely. The temperature ranges are preferably −20° C. to −90° C. The reaction mixtures can be worked up by the addition of water. The reaction products can be isolated while obtaining protective groups such as ketals or enol ethers etc. These aqueous preparations are advantageously effected at temperatures ≦ −10° C. in pH ranges ≧ pH 6. The pH can also be adjusted by the additions of salts such as NH$_4$Cl, NH$_4$OAc, NaH$_2$pO$_4$ or also acids.

However, the preparation can also be carried out in such a way that the dissolution of the reaction mixtures, i.e. the destruction of the surplus lithium organyl, is effected with the addition of water and acids or diluted acids and at pH ranges ≦ pH 6 and, in so doing, protective groupings such as ketals, enol ethers etc. which are possibly present in the molecule are split. In this case, inorganic acids, e.g. HCl, H$_3$PO$_4$ etc. or also organic acids, e.g. acetic acid, oxalic acid, p-toluenesulfonic acid etc. are used as acids.

The preparation can proceed generally in such a way that the decomposition of the surplus Li-organyl can be begun at low temperatures and the acid hydrolysis can then be continued at temperature of up to 50° C. The isolation of the reaction products can be effected by extraction or precipitation, but it is advantageous to distill off the solvent mixture from the reaction mixture in a vacuum and to isolate the highly pure crystals which occur in this process or by addition of alcohol or ketone.

The following compounds were synthesized with this process:

13-methyl-17α-cyanomethyl-17β-hydroxy-5(10),15-gonadiene-3-one 13-methyl-17α-cyanomethyl-17β-hydroxy-4,15-gonadiene-3-one 13-methyl-17α-cyanomethyl-3,17β-dihydroxy-gona-1,3,5(10),15-tetraene 13-methyl-3-methoxy-17α-cyanomethyl-17β-hydroxy-gona-1,3,5(10),15-tetraene 13-methyl-3-methoxy-17α-cyanomethyl-17β-hydroxy-gona-3,5(10),15-triene 13-methyl-3,3-dialkoxy-17α-cyanomethyl-17β-hydroxy-gona-5(10),15-diene 13-methyl-3,3-ethylenedioxy-17α-cyanomethyl-17β-hydroxy-gona-5(10),15-diene 13-ethyl-17α-cyanomethyl-17β-hydroxy-5(10),15-gonadiene-3-one 13-ethyl-17α-cyanomethyl-17β-hydroxy-4,15-gonadiene-3-one 13-ethyl-17α-cyanomethyl-3,17β-dihydroxy-gona-1,3,5(10),15-tetraene 13-ethyl-3-methoxy-17α-cyanomethyl-17β-hydroxy-gona-1,3,5(10),15-tetraene 13-ethyl-3-methoxy-17α-cyanomethyl-17β-hydroxy-gona-3,5(10),15-triene 13-ethyl-3,3-dialkoxy-17α-cyanomethyl-17β-hydroxy-gona-5(10),15-diene 13-ethyl-3,3-ethylenedioxy-17α-cyanomethyl-17β-hydroxy-gona-5(10),15-diene The use of the new process, the one-step introduction of the cyanomethyl group into the 17α-position of the steroid molecule, provides the preconditions for an environmentally sound synthesis which can be implemented technically. The known environmental loading is prevented with this new process, since the solvents are extensively recovered, the lithium salt occurring in the preparation can be separated out favorably, and the residual amounts of acetonitrile contained in the waste water are biodegradable in diluted solutions (Martinez, "Immobilization, Detoxification and Destruction of Chemicals" [Immobilisation, Entgiftung und Zerstörung von Chemikalien], 1st edition, Verlag Harri Deutsch, Thun-Frankfurt/Main, page 211).

EXAMPLE 1

2-Methoxy-13-ethyl-17α-cyanomethyl-17β-hydroxy-3,5,15-gonatriene 9.5 ml butyllithium solution (1.4.5 mmoles butyllithium) are placed in a reaction vessel in inert gas, cooled to temperatures $< -60°$ C. and then mixed with 10.0 ml purified, dry tetrahydrofuran. 0.78 ml acetonitrile (15 mmoles) are added to this solution accompanied by stirring and cooling. A solution of 2g 3-methoxy-13-ethyl-3,5,15-gonatriene-17-one (6.7 moles) is then added in 10 ml tetrahydrofuran in such a way that the reaction temperature of $-60°$ C. is not exceeded. After adding the steroid solution, subsequent reaction is allowed to take place for another hour, the temperature of the reaction mixture is allowed to rise to approximately $-10°$ C. and 10 ml water is added to it by drops beginning at this temperature. The temperature of the reaction mixture can rise to $+10°$ C. The phases are separated, the organic phase is reduced and the residue is crystallized with methanol.

Yield: 1.8 g = 79% of theory

Flame point: 195.2° C. to 197.5° C.

$^1$H-NMR spectrum: (80 MHz, CDCl$_3$, δ against TMS as inner standard) 0.90 ppm (tr, 3H, J=7 Hz, 18—CH$_2$—CH$_3$); 2.54 ppm (s, 2H, 17α—CH$_2$—CN); 3.28 ppm (s, 3H, 3—OCH$_3$); 5.23 ppm (s, 1H, 4-CH); 5.30 ppm (m, 1H, 6—CH); 5.74 ppm (dd, 1H, J=6 Hz and 3 Hz, 15—CH); 6.00 ppm (d, 1H, J=6 Hz, 16—CH).

EXAMPLE 2

13-Ethyl-17α-cyanomethyl-17β-hydroxy-4,15-gonadiene-3-one

According to the process described in Example 1, 2 g of 3-methoxy-13-ethyl-3,5,15-gonatriene-17-one is converted to 3-methoxy-13-ethyl-17α-cyanomethyl-17β-hydroxy-3,5,15-gonatriene at reaction temperatures $< -35°$ C. After the subsequent reaction the reaction mixture is mixed with diluted sulfuric acid at temperatures beginning at approximately $-15°$ C. The temperature of the reaction mixture can rise to 25° C. After separating the aqueous phase, the organic phase is reduced in a vacuum and crystallized with the addition of methanol. After crystallization, it is stirred for up to 1 hour and then cooled to approximately 10° C. and the resultant crystals are filtered with suction.

$^1$H=-NMR spectrum: (80 MHz, CDCl$_3$, δ against TMS as inner standard) 0.94 ppm (tr, 3H, J=7 Hz, 18—CH$_2$—CH$_3$); 2.55 ppm (s, 17α—CH$_2$—CN); 5.78 ppm (dd, 1H, J=6 and 3 Hz, 15—CH); 5.89 ppm (s, 1H, 4—CH); 6.03 ppm (d, 1H, J=6 Hz, 16—CH).

EXAMPLE 3

3-Methoxy-17α-cyanomethyl-17β-hydroxy-1,3,5(10),15-estratetraene 27.7 ml butyllithium solution (0.0443 moles) are added to a sulfurating flask in inert gas and cooled to $-60°$ C. accompanied by stirring. At this temperature, 15 ml tetrahydrofuran and 2.5 ml acetonitrile are added one after the other in such a way that the temperature of the reaction mixture does not exceed $-60°$ C. 5.0 g Δ 15-estrone-3-methylether are dissolved and suspended in 20 ml tetrahydrofuran and added to the reaction mixture in such a way that the temperature of the reaction mixture does not exceed $-40°$ C. during the addition. After adding the steroid mixture, subsequent reaction is allowed to take place at the above-indicated temperature for up to 1 hour, the temperature is allowed to rise to $-20°$ C. and the reaction mixture is then dissolved by adding 20 ml water and is adjusted to the neutral point by the addition of diluted sulfuric acid. After the phase are separated, the organic phase is reduced in a vacuum. The obtained residue is crystallized from methanol and isolated.

Yield: 4.5 g $^1$H=NMR spectrum: (80 MHz, CDCl$_3$, δ against TMS as inner standard) 0.97 ppm (s, 3H, 18—CH$_3$); 2.58 ppm (d, 2H, 17α—CH$_2$CN); 3.80 ppm (s, 3H, 3—OCH$_3$); 5.82 ppm (dd, 1H, J=6 and 3 Hz, 15—CH); 6.16 ppm (d, 1H, J=6 Hz, 16—CH); 6.68 ppm (m, 1H, 4—CH); 6.78 ppm ( dd, 1H, 2—CH); 7.21 ppm ( d, 1H, 1—CH).

EXAMPLE 4

13-Ethyl-17α-cyanomethyl-17β-hydroxy-4,15-gonadiene-3-one

According to the process described in Example 1, 4.0 g 3,3-(propylene-1,3-dioxy)-13-ethyl-5, 15-gonadiene-17-one are converted with a mixture of butyllithium, tetrahydrofuran and acetonitrile at temperatures $< -35°$ C. After acid hydrolysis and extraction with CHCl$_3$, 2.9 g of product crystals are isolated.

EXAMPLE 5

3,3-Dimethoxy-17α-cyanomethyl-17β-hydroxy-5(10)-estren 42 ml butyllithium solution (68mmoles butyllithium) are placed in a reaction vessel rinsed with inert gas and diluted with 25 ml purified, dry tetrahydrofuran at a temperature < −60° C. 3.5 ml acetonitrile (68 mmoles) are then added to the almost clear solution at temperatures < −60° C. accompanied by stirring and cooling. After the acetonitrile has been added, a solution of 5 g 3,3-dimethoxy-5(10)-estren-17-one (23 mmoles) in 25 ml tetrahydrofuran is added to the obtained suspension. The addition has been effected in such a way that the reaction temperature is maintained < −40° C. After a subsequent reaction time of 30 min the reaction solution is heated and 20 ml water is added to the mixture by drops at a temperature of 0° C. to 10° C. The obtained two-phase system is separated and the organic phase is reduced in a vacuum. The raw product is then dissolved in 40 ml chloroform and the organic phase is washed three times with 20 ml water. After reducing again, 5.4 g yellow oil (95% of theory) is obtained. DC tests resulted in a uniform product.

EXAMPLE 6

17α-Cyanomethyl-17β-hydroxy-5(10)-estren-3-one 5 g of 3,3-ethylenedioxy-5(10)-estren-17-one is converted to 17α-cyanomethyl-3,3-ethylenedioxy-17β-hydroxy-5(10)-estren corresponding to the test implementation mentioned in Example 1. After the subsequent reaction time, it is mixed with diluted $H_2SO_4$ and stirred intensively for 30 min at room temperature. After the phases are separated the organic phase is reduced and the obtained yellow oil is crytallized with the aid of acetone. 4.55 g (92% of theory) of 17α-cyanomethyl-17β-hydroxy-5(10)-estren-3-one are obtained.

Flame point: 175.7° C. to 177.4° C.

$^1$H-NMR spectrum: (80 HMz, $CDCl_3$, δ against TMS as inner standard) 0.98 ppm (s, 3H, 18—$CH_3$); 2.46 ppm (m, 4H, 1—$CH_2$, 3—$CH_2$); 2.63 ppm (m, 2H, 17α—$CH_2CN$); 2.76 ppm (m, 2H, 4—$CH_2$).

EXAMPLE 7

17α-Cyanomethyl-17β-hydroxyandrosten-3-one 10 ml butyllithium solution (13mmoles butyllithium) are placed in the reaction vessel with an inert gas flow and cooled. At temperatures < −60° C. the solution is mixed with 10 ml tetrahydrofuran and subsequently with 0.75 ml acetonitrile (14 mmoles). A solution of 1.9 g 3-methoxy-3,5-androstadiene-17-one (6.3 moles) in 10 ml tetrahydrofuran is added to the obtained suspension in such a way that the reaction temperature does not exceed −30° C. Further preparation is effected as in Example 1. The obtained product is subsequently converted in the methanol with the addition of acid to form17α-cyanomethyl-17β-hydroxy-4-androsten-3-one. 1.85 g (85% of theory) crystals are obtained.

Flame point: 278.8° C. to 281.1° C.

$^1$H-NMR spectrum: (80 MHz, $CDCl_3$, δ against TMS as inner standard) 0.98 ppm (s, 3H, 18—$CH_3$); 1.25 ppm (s, 5H, 19—$CH_3$); 2.52 and 2.63 ppm (d, 2H, 17α—$CH_2CN$); 5.76 ppm (s, 1H, 4—CH)

EXAMPLE 8

17α-Cyanomethyl-3,17β-dihydroxy-5-androsten 20 ml butyllithium is added to a reaction vessel in inert gas, cooled to approximately −70° C. and mixed with 20 ml tetrahydrofuran. 1.5 ml acetonitrile in 10 ml tetrahydrofuran is added to this solution accompanied by stirring and cooling. A solution of 3.6 g androstenolone in 30 ml tetrahydrofuran is hen added in such a way that the reaction temperature of −60° C. is not exceeded. After the addition of the steroid solution, a subsequent reaction is effected up to 1 hour, the temperature is allowed to rise to approximately 10° C. and the mixture is then added to water accompanied by stirring. The reaction product is extracted with chloroform, the $CHCl_3$ phases are washed repeatedly with water and then reduced as far as possible in a vacuum. The residue is then crystallized from $CHCl_3$.

Flame point: 214.7° C. to 214.9° C.

$^1$H-NMR spectrum: (80 MHz, $CDCl_3$, δ against TMS as inner standard) 0.81 ppm (s, 3H, 18—$CH_3$); 0.99 ppm (s, 3H, 19—$CH_3$); 2.63 ppm (s, 2H, 17α—$CH_2CN$)).

EXAMPLE 9

3-Methoxy-17α-cyanomethyl-17-hydroxy-1,3,5(10)-estratriene 13 ml butylllithium (20 mmoles) are cooled to < −60° C. in inert gas while stirring and mixed with 15 ml tetrahydrofuran. After adding 1.1 ml acetonitrile (20 mmoles) at a reaction temperature of < −60° C., a white suspension is obtained. 2.5 g estrone-3-methylether are suspended and partially dissolved in 20 ml tetrahydrofuran and added to the reaction solution in such a way that a temperature of −60° C. is not exceeded. After 30 min of stirring at < −60° C., it is dissolved with 20 ml water. The phases are separated and the organic phase is reduced in a vacuum. The 17α-cyanomethyl-17β-hydroxy-1,3,5(10)-estratriene-3-methylether crystallizes from a mixture of acetone and water with a yield of 78% of theory.

Flame point 149.2° C. to 149.9° C.

$^1$H-NMR spectrum: (80 MHz, $CDCl_3$, δ against TMS as inner standard) 0.95 ppm (s, 3H, 18—$CH_3$); 2.59 ppm (d, 1H, J=16 Hz, 17α—$CH_2CN$); 2.69 ppm (d, 1H, J=16 Hz, 17α—$CH_2CN$); 3.80 ppm (s, 3H, 3—$OCH_3$); 6.68 ppm (m, 1H, 4—CH); 6.72 ppm (dd, 1H, J=2 and 9 Hz); 7.22 ppm (d, 1H, J=9 Hz, 1 CH).

EXAMPLE 10

3-Methoxy-13-ethyl-17α-cyanomethyl-17β-hydroxy-3,5-gonadiene 10 ml butyllithium solution (0,028 moles butyllithium) are added to a reaction vessel in inert gas, cooled to temperatures < −35° C. and then mixed with 30 ml purified, dry tetrahydrofuran. 1.15 ml aceetonitrile (0,022 moles) are added to this solution accompanied by stirring and cooling. A solution of 3.0 g 3-methoxy-13-ethyl-3,5-gonadiene-17-one (0.01 mole) in 25 ml tetrahydrofuran is then added in such a way that the reaction temperature of −30° C. is not exceeded. After adding the steroid solution, subsequent reaction is carried out for another 30 min, the temperature of the reaction mixture is then allowed to rise to approximately −10° C. and 50 ml water are added to it by drops at this temperature. The reaction temperature can rise to +10° C. The obtained two-phase mixture is separated and the organic phase is reduced in a vacuum. The obtained residue is absorbed in chloroform, the $CHCl_3$ solution is washed to neutral point with water, dried over $Na_2SO_4$, and then reduced as far as possible in a vacuum.

Yield: 69%

Flame point: 192.7° C.

¹H-NMR spectrum: (80 MHz, CDCl₃, δ against TMS as inner standard) 1.04 ppm (tr, 3H, J=7 Hz, 18—CH₂—CH₃); 2.53 ppm (d, 1H, J=16 Hz, 17—CH₂CN); 2,68 ppm (d, 1H, J=16 Hz, 17—CH₂CN); 3.60 ppm (s, 3H, 3—OCH₃); 5.25 ppm (s, 1H, 4—CH); 5.28 ppm (m, 1H, 6—CH)

EXAMPLE 11

13-Methyl-17α-cyanomethyl-17β-hydroxy-4-gonen-3-one 3.0 g 3-methoxy-13-methyl-3,5-gonadiene-17-one are converted in a manner analogous to that in Example 6.

Yield: 74% of theory
Flame point: 243° to 246° C.

¹H-NMR spectrum: (80 MHz, CDCl₃, δ against TMS as inner standard) 0.84 ppm (s, 3H, 18—CH₃); 2.63 ppm (2d, 2H 17α—CH₂CN); 5.75 ppm (s, 1H, 4—CH).

EXAMPLE 12

17α-Cyanomethyl-17β-hydroxy-13-methyl-5(10),9(11)-gonadiene-3-one 36 ml butyllithium solution (1.3 moles/1) are placed in a reaction vessel rinsed with inert gas and diluted with 10 ml tetrahydrofuran at −60° C. 3 ml acetonitrile are then added to this solution accompanied by stirring and cooling in such a way that the temperature of −60° C. is not exceeded. A solution of 2.5 g 13-methyl-3,3-dimethoxy-5(10),9(11)-gonadiene-17-one in 20 ml tetrahydrofuran is then added by drops to this reaction mixture in such a way that the above-indicated temperature range is not exceeded. After adding the substance, the reaction mixture is stirred for 30 min, the temperature is allowed to rise to +−0° C, diluted sulfuric acid is added to the reaction mixture by drops and the reaction mixture is stirred for another 30 min at room temperature. The aqueous phase is then separated off, reextracted two times with methylene chloride, the unified organic phase is washed free of acid and then reduced in a vacuum. The distillation residue is mixed with acetone for crystallization and the crystalline product is removed by suction after standing overnight.

¹H-NMR spectrum: (80 MHz, CDCl₃, δ against TMS as inner standard) 0.93 ppm (s, 3H, 18—CH₃); 2.56 ppm (m, 6H, 1—CH₂, 2—CH₂, 17α—CH₂CN); 2.90 ppm (m, 2H, 4—CH₂); 5.65 ppm (m, 1H, 11—CH)

EXAMPLE 13

3-Ethyl-17α-cyanomethyl-17β-hydroxy-4,9-gonadiene-3-one 6.5 ml butyllithium solution, 10 ml THF, 1.8 ml acetonitrile are reacted with 13-ethyl-3,3-ethylenedioxy-5(10),9(11)-gonadiene-17-one at temperatures ≦−30° C. and with subsequent dissolution with 30 ml water to form 13-ethyl-3,3-ethylenedioxy-17α-cyanomethyl-17β-hydroxy-5(10),9(11)-gonadiene according to the process described in Example 1. Isolation of the product and reaction with concentrated hydrochloric acid in ethanol after CHCl₃ extraction, reduction and crystallization from ethanol/water results in 13—ethyl-17α-cyanomethyl-17β-hydroxy-4,9-gonadiene-3-one.

Yield: 56% of theory
Flame point: 214° C. to 215° C.

¹H-NMR spectrum: (80 MHz, CDCl₃, δ against TMS as inner standard) 1.16 ppm (tr, 3H, J=7 Hz, 18—CH₂—CH₃); 2.53 ppm (d, 1H, J=16 Hz, 17—CH₂CN); 2.68 ppm (d, 1H, J=16 Hz, 17—CH₂CN); 5.78 ppm (s, 1H 4—CH)

EXAMPLE 14

13-Methyl-17α-cyanomethyl-17β-hydroxy-4,9-gonadiene-3-one.

16.5 ml butyllithium solution are placed in a reaction vessel in inert gas, cooled to temperatures <−35° C. and mixed with 15 ml tetrahydrofuran. 1.8 ml acetonitrile/10 ml tetrahydrofuran are added to this solution. A solution of 5 g 3,3-(1,3-propylenedioxy)-13-methyl-5(10),9(11)-gonadiene-17-one is then added in 30 ml THF and the reaction mixture is kept at a temperature of ≦−35° C. for up to one hour, the reaction mixture is then dissolved with 40 ml water and the organic phase is isolated. The organic phase is reduced, absorbed in ethanol, mixed with 1 ml concentrated HCl and stirred for 2 hours at room temperature, the solution is reduced and the obtained crystallisate is isolated.

Yield: 4.0 g
Flame point: 208° C. to 211.5° C.

¹H-NMR spectrum: (80 MHz, CDCl₃, δ against TMS as inner standard) 1.09 ppm (s, 3H, 18—CH₃); 2.47 ppm (s, 4H,1 CH₂ and 2 (CH₂); 2.52 ppm (s, 1H, J=16.4 Hz, 17—CH₂CN); 2.63 ppm (s, 1H, J=16.4 Hz, 17—CH₂CN); 5.71 ppm (s, 1, H, 4—CH).

EXAMPLE 15

13-methyl-17α-cyanomethyl-17β-hydroxy-4,9,11-gonatriene-3-one 20 ml n-butyllithium solution (26 mmoles) are placed in a reaction vessel in an inert gas flow and cooled. At temperatures of −40° C. the solution is mixed with 20 ml methyl-t.-butyl ether and then with 1.5 ml acetonitrile. A solution of 3.8 g of 3,3-ethylenedioxy-13-methyl-4,9,11-genatriene-17-one in 20 ml methyl-t.-butyl ether is added to the obtained suspension in such a way that the reaction temperature does not exceed −25° C. Continued preparation is effected as in Example 1. The obtained product is then converted in methanol with the addition of acid at pH 2.5 to 13-methyl-17α-cyanomethyl-17β-hydroxy-4,9,11-gonatriene.

Yield: 2.38 g (63.3%)
flame point: 152° C. to 155° C.

EXAMPLE 16

13-Ethyl-17α-cyanomethyl-17β-hydroxy-4,9,11-gonatriene-3-one 1.95 g 3,3-ethylenedioxy-13-ethyl-4,9,11-gonatriene-17-one is converted to 0.89 13-ethyl-17α-cyanomethyl-17β-hydroxy-4,9,11-gonatriene-3-one according to the process described in Example 15.

Flame point: 193° C. to 195° C.

While the invention has been illustrated and described as embodied in a process for production of unsaturated 17α-cyanomethyl-17β-hydroxy steroids, it is not intended to be limited to the details shown, since various modifications and structural changes may be made without departing in any way from the spirit of the present invention.

The embodiments of the invention in which an exclusive property or privilege is claimed are defined as follows:

1. Unsaturated 15-dehydro-17α-cyanomethyl-17β-hydroxy steroids of the formula

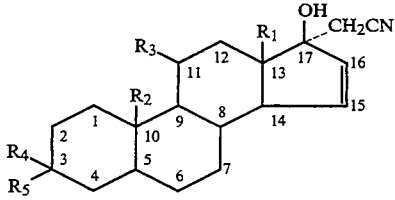

wherein

R₁ is methyl or ethyl;

R₂ is selected from the group consisting of hydrogen and methyl;

R₃ is selected from the group consisting of hydrogen, hydroxy, acetoxy and alkoxy having 1 to 6 carbon atoms;

R₄ is hydrogen and R₅ is selected from the group consisting of hydroxy, acetoxy and alkoxy having 1 to 6 carbon atoms, or R₄ and R₅ are both methoxy or both ethoxy, or R₄ and R₅, together, represent a keto group or a ketal group selected from the group consisting of —O—CH₂—CH₂—O—; —O—CH₂—C(CH₃)₂—CH₂—O— and —OPCH(CH₃)—CH₂—CH(CH₃)—O—;

wherein said steroids of formula (I) also have at least one other double bond between the 1 and 2 positions, the 2 and 3 positions, the 3 and 4 positions, the 4 and 5 positions, the 5 and 6 positions, the 5 and 10 positions, the 9 and 10 positions and the 9 and 11 positions, said 1,2,3,4,5,6,9,10 and 11 positions being shown in the formula I above; and with the proviso that R₂ cannot be methyl, when said at least one other double bond is between the 5 and 10 positions or between the 9 and 10 positions.

2. Asteroid according to claim 1, consisting of 13-methyl-17α-cyanomethyl-17β-hydroxy-5(10),15-gonadien-3-one.

3. Asteroid according to claim 1, consisting of 13-methyl-17α-cyanomethyl-17β-hydroxy-4,15-gonadien-3-one.

4. Asteroid according to claim 1, consisting of 13-methyl-17α-cyanomethyl-3,17β-dihydroxy-gona-1,3,5(10),15-tetraene.

5. Asteroid according to claim 1, consisting of 13-methyl-3-methoxy-17α-cyanomethyl-17β-hydroxy-gona -1,3,5(10),15-tetraene.

6. Asteroid according to claim 1, consisting of 13-methYl-3-methoxy-17α-cyanomethyl-17β-hydroxy-gona-3,5(10)15-triene.

7. Asteroid according to claim 1, consisting of 13-methyl-3,3-dialkoxy-17α-cyanomethyl-17β-hydroxy-gona -5(10),15-diene, wherein said alkoxy groups have 1 to 6 carbon atoms.

8. Asteroid according to claim 1, consisting of 13-methyl-3,3-ethylenedioxy-17α-cyanomethyl-17β-hydroxy-gona-5(10),15-diene.

9. Asteroid according to claim 1, consisting of 13-ethyl-17α-cyanomethyl-17β-hydroxy-5(10),15-gonadien-3-one.

10. Asteroid according to claim 1, consisting of 13-ethyl-17α-cyanomethyl-17β-hydroxy-4,15-gonadien-3-one.

11. Asteroid according to claim 1, consisting of 13-ethyl-17α-cyanomethyl-3,17β-dihydroxy-gona-1,3,5(10), 15-tetraene.

12. Asteroid according to claim 1, consisting of 13-ethyl-3-methoxy-17α-cyanomethyl-17β-hydroxy-gona -1,3,5(10),15-tetraene.

13. Asteroid according to claim 1, consisting of 13-ethyl-3-methoxy-17α-cyanomethyl-17β-hydroxy-gona-3,5(10),15-triene.

14. Asteroid according to claim 1, consisting of 13-ethyl-3,3-dialkoxy-17α-cyanomethyl-17β-hydroxy-gona -5(10),15-diene.

15. Asteroid according to claim 1, consisting of 13-ethyl-3,3-ethylenedioxy-17α-cyanomethyl-17β-hydroxy-gona -5(10),15-diene.

16. Unsaturated 15-dehydro-17α-cyanomethyl-17β-hydroxy steroids selected from the group consisting of 13-methyl-17α-cyanomethyl-17β-hydroxy-5(10),15-gonadien-3-one, 13-methyl-17α-cyanomethyl-17β-hydroxy-4,15-gonadien-3-one, 13-methyl-17α-cyanomethyl-3,17β-dihydroxy-gona-1,3,5(10),15-tetraene, 13-methyl-3-methoxy-17α-cyanomethyl-17β-hydroxy-gona-1,3,5(10),15-tetraene, 13-methyl-3-methoxy-17α-cyanomethyl-17β-hydroxy-gona-3,5(10),15-triene,13-methyl -3,3-dialkoxy-17α-cyanomethyl-17β-hydroxy-gona-5(10),15-diene, 13-methyl-3,3-ethylenedioxy-17α-cyanomethyl-17β-hydroxy-gona-5(10)-diene, 13-ethyl-17α-cyanomethyl-17α-hydroxy-5(10),15-gonadien-3-one, 13-ethyl-17α-cyanomethyl-17β-hydroxy-4,15-gonadien-3-one, 13-ethyl-17α-cyanomethyl-3,17β-dihydroxy-gona-1,3,5(10),15-tetraene, 13-ethyl-3-methoxy-17α-cyanomethyl-17β-hydroxy-gona,1,3,5(10),15-tetraene, 13-ethyl-3-methoxy-17α-cyanomethyl-17β-hydroxy-gona-3,5(10),15-triene, 13-ethyl-3,3-dialkoxy-17α-cyanomethyl-17β-hydroxy-gona-5(10),15-diene, and 13-ethyl-3,3-ethylenedioxy-17α-cyanomethyl-17β-hydroxy-gona-5(10),15-diene.

17. Pharmaceutical composition comprising a therapeutically effective amount of an unsaturated steroid as defined in claim 1 in a pharmaceutically acceptable carrier.

18. Pharmaceutical composition comprising a therapeutically effective amount of an unsaturated steroid as defined in claim 16 in a pharmaceutically acceptable carrier.

19. Pharmaceutical composition as defined in claim 18, further comprising ethinyl estradiol.

20. Process for making an unsaturated 15-dehydro-17α-cyanomethyl-17β-hydroxy steroid of the formula I:

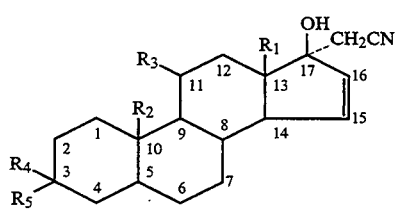

wherein

R₁ is methyl or ethyl;

R₂ is selected from the group consisting of hydrogen and methyl;

R₃ is selected from the group consisting of hydrogen, hydroxy, acetoxy and alkoxy having 1 to 6 carbon atoms;

R₄ is hydrogen and R₅ is selected from the group consisting of hydroxy, acetoxy and alkoxy having 1 to 6 carbon atoms, or R₄ and R₅ are both methoxy or both ethoxy, or R₄ and R₅, together, represent a keto group or a ketal group selected from the group consisting of —O—CH₂—CH₂—O—; —O—CH₂—C(CH₃)₂—CH₂—O—; and —OCH(CH₃)—CH₂—CH(CH₃)—O—;

wherein said steroids of formula (I) also have at least one other double bond between the 1 and 2 positions, the 2 and 3 positions, the 3 and 4 positions, the 4 and 5 positions, the 5 and 6 positions, the 5 and 10 positions, the 9 and 10 positions and the 9 and 11 positions, said 1,2,3,4,5,6,9,10 and 11 positions being shown in formula I above; and with the proviso that R₂ cannot be methyl, when said at least one other double bond is between 5 and 10 positions or the 9 and 10 positions; comprising the steps of:

a) forming Li—CH₂CN in an inert organic solvent by reacting acetonitrile with a lithium compound selected from the group consisting of lithium alkyl compounds having alkyl groups containing from one to six carbon atoms and lithium dialkyl compounds having alkyl groups containing from one to six carbon atoms in the inert organic solvent;

b) after step a), reacting an unsaturated 17-ketosteroid of the formula II:

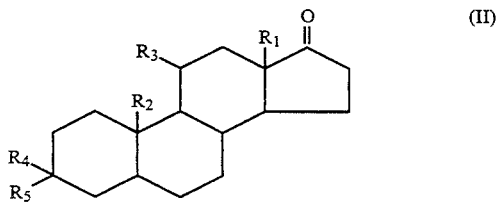

with the Li—CH₂CN contained in the inert organic solvent to form a reaction mixture, said R₁, R₂, R₃, R₄ and R₅ being the same as in said formula I; and c) after step b), hydrolyzing the reaction mixture to obtain the unsaturated steroid of formula (I).

21. Process as defined in claim 20, wherein the inert organic solvent is selected from the group consisting of aromatic hydrocarbons, aliphatic hydrocarbons, ethers, tertiary amines and mixtures thereof.

22. Process as defined in claim 21, wherein the tertiary amines are selected from the group consisting of triethylamine, diisopropylamine, pyridine and tetraalkyl ethylenediamine.

23. Process as defined in claim 21, wherein the ethers are selected from the group consisting of diethyl ether, diisopropyl ether, tetrahydrofuran, dioxane, anisole, dimethoxyethane, diethoxyethane and methyl-t-butyl ether.

24. Process as defined in claim 21, wherein the aromatic hydrocarbons are selected from the group consisting of benzene and toluene.

25. Process as defined in claim 21, wherein the aliphatic hydrocarbons are selected from the group consisting of pentane, hexane and heptane.

26. Process as defined in claim 20, wherein during the reacting step b) one mole of the unsaturated 17-ketosteroid of the formula II is added to the inert organic solvent containing the Li—CH₂CN for each 1 to 5 moles of the acetonitrile used to form the Li—CH₂CN.

27. Process as defined in claim 20, wherein the reacting step b) is performed at a reaction temperature of −20° C. to −90 ° C.

28. Process as defined in claim 20, wherein the hydrolyzing step c) is performed by adding water to the reaction mixture at hydrolysis temperatures of less than −10° C. and at pH values greater than 6.

29. Process as defined in claim 28, further comprising adjusting the pH values by addition of a member selected from the group consisting of salts and acids.

30. Process as defined in claim 29, wherein the salt is selected from the group consisting of ammonium acetate and ammonium phosphate.

31. Process as defined in claim 20, wherein the hydrolyzing step c) is performed, at least in part, by adding an aqueous acid solution to the reaction mixture to form the unsaturated steroid of formula (I) above, and wherein the hydrolyzing step c) is performed at a pH value of less than 6 and at hydrolysis temperatures of up to 50° C.

32. Process as defined in claim 31, further comprising adjusting the pH values by addition of a member selected from the group consisting of salts and acids.

33. Process as defined in claim 32, wherein said acids are selected from the group consisting of HCl, H₃PO₄, H₂SO₄, HClO₄, acetic acid, oxalic acid and toluene sulfonic acid.

* * * * *